(12) United States Patent
Harada et al.

(10) Patent No.: US 9,861,716 B2
(45) Date of Patent: Jan. 9, 2018

(54) STERILIZING METHOD

(71) Applicant: Toyo Seikan Co., Ltd., Tokyo (JP)

(72) Inventors: Takaaki Harada, Yokohama (JP);
Takeshi Iwashita, Yokohama (JP);
Kenichi Kominami, Yokohama (JP)

(73) Assignee: Toyo Seikan Co., Ltd., Tokyo (JP)

( * ) Notice: Subject to any disclaimer, the term of this patent is extended or adjusted under 35 U.S.C. 154(b) by 23 days.

(21) Appl. No.: 14/895,084

(22) PCT Filed: Jul. 11, 2014

(86) PCT No.: PCT/JP2014/068568
§ 371 (c)(1),
(2) Date: Dec. 1, 2015

(87) PCT Pub. No.: WO2015/012127
PCT Pub. Date: Jan. 29, 2015

(65) Prior Publication Data
US 2016/0121010 A1 May 5, 2016

(30) Foreign Application Priority Data

Jul. 26, 2013 (JP) ................. 2013-155296

(51) Int. Cl.
*A61L 2/18* (2006.01)
*A61L 2/20* (2006.01)
(52) U.S. Cl.
CPC ............ *A61L 2/186* (2013.01); *A61L 2/208* (2013.01)
(58) Field of Classification Search
CPC ..................................... A61L 2/186
See application file for complete search history.

(56) References Cited

U.S. PATENT DOCUMENTS

2009/0269324 A1  10/2009  Herdt et al.
2009/0311134 A1  12/2009  Iwashita et al.
(Continued)

FOREIGN PATENT DOCUMENTS

JP    08-058744 A     3/1996
JP    11-342919 A    12/1999
(Continued)

OTHER PUBLICATIONS

International Search Report of PCT/JP2014/068568 dated Oct. 14, 2014.
(Continued)

*Primary Examiner* — Donald Spamer
(74) *Attorney, Agent, or Firm* — Sughrue Mion, PLLC

(57) ABSTRACT

A method of sterilizing containers by using a peracetic acid-type sterilizing composition solution, wherein the sterilizing composition solution containing peracetic acid, hydrogen peroxide, acetic acid and catalase as prepared in a circulating tank (1) is heated through a heating unit (3), fed to a sterilizing unit (4), and is recovered in the circulating tank (1) after it is used for the sterilization, wherein the catalase is added to the sterilizing composition solution in a circulating passage of after it was used for the sterilization but before it is fed to the heating unit. This makes it possible to suppress the catalase from losing its activity, to maintain the sterilizing power of the sterilizing composition solution, and to use the sterilizing composition solution in a circulating manner without cooling it saving, therefore, the heat energy providing advantage in economy.

4 Claims, 1 Drawing Sheet

PASSAGE DIAGRAM 1

(56) References Cited

U.S. PATENT DOCUMENTS

2011/0052445 A1    3/2011  Herdt et al.
2012/0321510 A1  12/2012  Herdt et al.

FOREIGN PATENT DOCUMENTS

| JP | 2009-291443 A | 12/2009 |
|----|---------------|---------|
| JP | 2011-517946 A | 6/2011 |
| JP | 2012-200456 A | 10/2012 |
| JP | 2013-503682 A | 2/2013 |
| WO | 2007/148410 A1 | 12/2007 |

OTHER PUBLICATIONS

Communication dated Feb. 3, 2017, from the European Patent Office in counterpart European Application No. 14828800.4.

PASSAGE DIAGRAM 1

PASSAGE DIAGRAM 2

STERILIZING METHOD

CROSS REFERENCE TO RELATED APPLICATIONS

This is a National Stage of International Application No. PCT/JP2014/068568 filed Jul. 11, 2014, claiming priority based on Japanese Patent Application No. 2013-155296 filed Jul. 26, 2013, the contents of all of which are incorporated herein by reference in their entirety.

TECHNICAL FIELD

This invention relates to a method of sterilizing the containers by using a peracetic acid-type sterilizing composition solution. More specifically, the invention relates to a sterilizing method capable of efficiently using the peracetic acid-type sterilizing composition solution in a circulating manner.

BACKGROUND ART

The peracetic acid-type sterilizer has heretofore been widely used for sterilizing or pasteurizing food containers and the like (patent document 1). The peracetic acid-type sterilizer contains peracetic acid, acetic acid and hydrogen peroxide in an equilibrium state. However, the hydrogen peroxide, if its concentration is too high, tends to remain in the container and, therefore, must be washed away after the sterilization to a sufficient degree with aseptic water. Therefore, there has also been proposed a pasteurizing method by using a sterilizing composition solution obtained by adding a catalase capable of decomposing hydrogen peroxide to the peracetic acid-type sterilizer (patent document 2).

In the sterilizing method that uses the peracetic acid-type sterilizing composition solution, it is a practice to recover the peracetic acid-type sterilizing composition solution used for the sterilization, adjust the concentration thereof, and circulate the sterilizing composition solution to the sterilizing equipment to use it again. The peracetic acid-type sterilizer, usually, exhibits good sterilizing efficiency at temperatures of not lower than 60° C. To conduct the sterilization, therefore, the peracetic acid-type sterilizing composition solution is used in a heated state. On the other hand, if the peracetic acid-type sterilizer or the peracetic acid-type sterilizing composition solution is placed in a heated state, decomposition of the peracetic acid is accelerated causing an increase in the amount of the hydrogen peroxide and, therefore, a decrease in the sterilizing power. In using the peracetic acid-type sterilizing composition solution in a circulating manner, therefore, it has been attempted to cool the peracetic acid-type sterilizing composition solution once heated for sterilization at a temperature of 60 to 70° C. down to 35° C. or lower through a circulation passage other than the sterilizing unit (patent documents 3 and 4).

PRIOR ART DOCUMENTS

Patent Documents

Patent document 1: JP-A-8-58744
Patent document 2: JP-T-2011-517946
Patent document 3: JP-A-2009-291443
Patent document 4: JP-A-2012-200456

OUTLINE OF THE INVENTION

Problems that the Invention is to Solve

The above-mentioned method of circulating the peracetic acid-type sterilizing composition solution, however, requires both heating and cooling the peracetic acid-type sterilizing composition solution accompanied, therefore, by poor heat energy efficiency and dissatisfaction in economy. Upon heating the peracetic acid-type sterilizing composition solution, further, decomposition of the peracetic acid is accelerated causing an increase in the amount of the hydrogen peroxide. Besides, the catalase that is added to the peracetic acid-type sterilizing composition solution for decomposing the hydrogen peroxide, is inactivated in the presence of the peracetic acid or under a high temperature condition. In other words, the catalase must be added in large amounts giving rise to the occurrence of problems such as foaming or generation of aggregated matters.

It is, therefore, an object of the present invention to provide a sterilizing method that can use the peracetic acid-type sterilizing composition solution in a circulating manner maintaining its sterilizing power while suppressing a decrease in the activity of the catalase.

Another object of the present invention is to provide a sterilizing method that can use the peracetic acid-type sterilizing composition solution in a circulating manner without cooling it, contributing to saving the heat energy and offering advantage in economy.

Means for Solving the Problems

According to the present invention, there is provided a sterilizing method in which a sterilizing composition solution containing peracetic acid, hydrogen peroxide, acetic acid and catalase as prepared in a circulating tank, is heated through a heating unit, fed to a sterilizing unit, and is recovered in the circulating tank after it is used for the sterilization, wherein the catalase is added to the sterilizing composition solution in a circulating passage of after it was used for the sterilization but before it is fed to the heating unit.

In the sterilizing method of the present invention, it is desired that:
1. The catalase is a catalase capable of decomposing the hydrogen peroxide by not less than 35% of its initial concentration 10 minutes after it has been added to the peracetic acid-type sterilizer adjusted at a temperature of 50° C. so as to have a peracetic acid concentration of 3000 ppm;
2. The sterilizing composition solution recovered from the sterilizing unit is recovered in the circulating tank without being cooled;
3. The catalase is added in the circulating tank; and
4. The sterilizing composition solution in the circulating tank has a peracetic acid concentration of 500 to 10,000 ppm and a hydrogen peroxide concentration of less than 500 ppm.

Effects of the Invention

In the sterilizing method of the present invention, the catalase is added in the circulating passage in which the sterilizing composition solution containing peracetic acid, hydrogen peroxide, acetic acid and catalase circulates excluding, however, the passage of from the heating unit in which the sterilizing composition solution is maintained at a high temperature up to the sterilizing unit. Therefore, the catalase is allowed to efficiently exhibit its capability for decomposing the hydrogen peroxide, and it is thus made possible to effectively prevent a decrease in the sterilizing power of the peracetic acid-type sterilizing composition solution.

With the catalase being added in the circulating passage, further, the catalase is prevented from losing its activity. Therefore, the catalase needs be added in decreased amounts, contributing to minimizing the foaming or the generation of aggregated matters caused by the addition of the catalase and, therefore, the containers need be washed to a minimum degree so as to be sterilized.

It is, further, made possible to eliminate the step of cooling that was so far necessary in the circulating passage owing to the features of the present invention, i.e., owing to a decrease in the temperature condition during the sterilization as a result of increasing the peracetic acid concentration in the sterilizing composition solution to improve the sterilizing power, and owing to the use of the catalase capable of decomposing the hydrogen peroxide by not less than 35% of its initial concentration 10 minutes after it has been added to the peracetic acid-type sterilizer adjusted at a temperature of 50° C. so as to have a peracetic acid concentration of 3000 ppm. It is, therefore, made possible to decrease the amount of heat energy that is used accompanying the circulation offering, therefore, advantage in economy.

MODES FOR CARRYING OUT THE INVENTION

As described above, if the concentration of the hydrogen peroxide increases, the peracetic acid-type sterilizing composition solution that chiefly contains a peracetic acid-type sterilizer comprising peracetic acid, acetic acid and hydrogen peroxide (hereinafter often referred to simply as "sterilizing composition solution"), exhibits a deceased sterilizing power and causes such a problem that the hydrogen peroxide tends to remain in the material (container) that is sterilized. Therefore, attempts have been made to add the catalase to decompose the hydrogen peroxide to thereby control the hydrogen peroxide concentration and to stably maintain the sterilizing power for extended periods of time. To efficiently conduct the sterilization by using the peracetic acid-type sterilizing composition solution, on the other hand, though dependent upon the composition of the sterilizing composition solution, it is desired to heat the sterilizing composition solution at a temperature of, usually, not lower than 50° C. Therefore, the sterilizing composition solution is maintained at a high temperature in the passage of at least from the heating unit in the circulating passage up to the sterilizing unit, and it is not efficient to add the catalase in the above passage since the catalase is subject to be deactivated under high-temperature conditions.

In the sterilizing method of the present invention, the catalase is added to the sterilizing composition solution in the passage of from just after the sterilizing composition solution is used in the sterilizing unit but before it is fed to the heating unit in the circulation passage of the sterilizing composition solution. This enables the catalase to effectively exhibit its activity and to maintain the sterilizing power of the peracetic acid-type sterilizing composition solution.

To suppress the catalase added to the sterilizing composition solution from being deactivated, attempts can be made to cool the sterilizing composition solution after it is used for the sterilization to lower the temperature of the sterilizing composition solution. In this case, however, the sterilizing composition solution is heated and cooled repetitively, which is a disadvantage in economy.

Therefore, the present invention uses the peracetic acid-type sterilizing composition solution that has a high peracetic acid concentration and employs a low-temperature condition for the sterilization making it possible to eliminate the step of cooling the sterilizing composition solution. Or as will be described later, the invention uses a catalase having excellent heat resistance and chemical resistance (resistance against the peracetic acid). Namely, the catalase is not deactivated even if it is added (supplemented) to the sterilizing composition solution of a high temperature making it, therefore, possible to eliminate the step of cooling.

(Circulation Passage)

Figure 1:
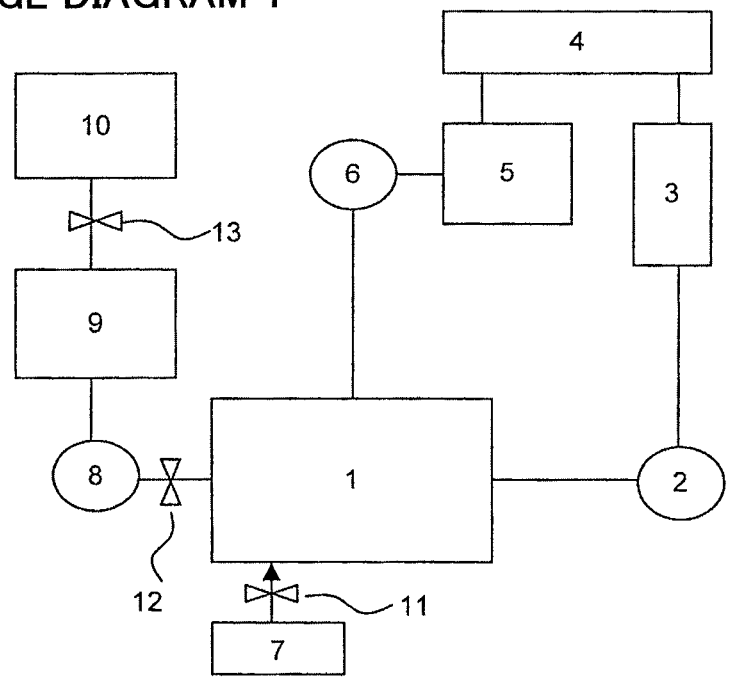
FIG. 1 is a drawing illustrating a circulating passage in a sterilizing method of the present invention.
Figure 2:
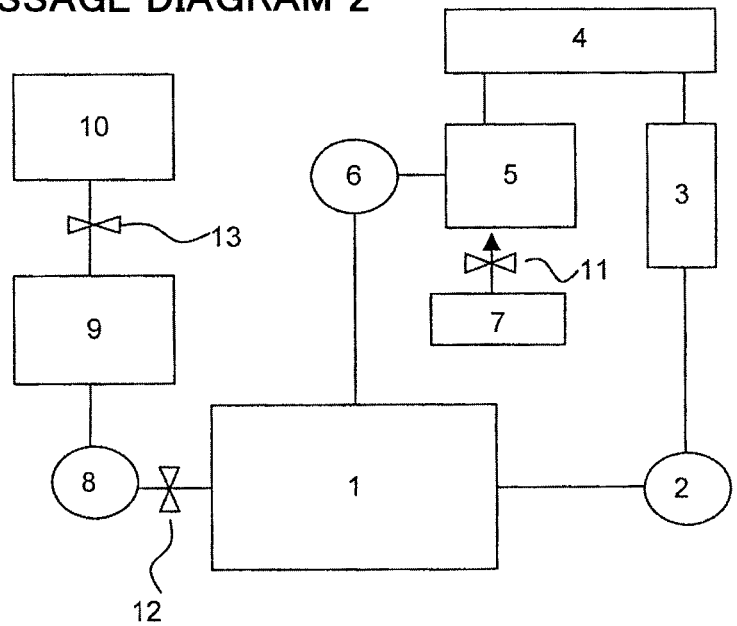
FIG. 2 is a drawing illustrating another circulating passage in the sterilizing method of the present invention.

A basic circulation passage of the sterilizing composition solution in the sterilizing method of the invention comprises, as shown in FIGS. 1 and 2, a circulating tank 1→a heating unit 3→a sterilizing unit 4→a recovery tank 5→the circulating tank 1. That is, the sterilizing composition solution is fed from the circulating tank 1 into the heating unit 3 through a feed pump 2. The sterilizing composition solution is heated at a desired temperature in the heating unit 3 and is then fed to the sterilizing unit 4. In the sterilizing unit 4, the sterilizing composition solution is injected onto the materials to be sterilized. The sterilizing composition solution after used is recovered in the recovering tank 5. The sterilizing composition solution is returned from the recovering tank 5 back to the circulating tank 1 through a feed pump 6.

The sterilizing composition solution is prepared in a preparation tank 10 located in a separate passage connected to the above circulation passage in such a manner that the peracetic acid and the hydrogen peroxide are contained therein at predetermined concentrations. The sterilizing composition solution is added such that the sterilizing composition solution is maintained at a predetermined concentration in the circulating tank 1. In the embodiments shown in FIGS. 1 and 2, the sterilizing composition solution prepared in the preparation tank 10 is once fed into a buffer tank 9 through a feed pump 8. From the buffer tank 9, the sterilizing composition solution is fed in a desired amount depending on the concentration of the sterilizing composition solution in the circulating tank 1. Here, valves 13 and 12 are provided between the preparation tank 10 and the buffer tank 9, and between the feed pump 8 and the circulating tank 1, respectively.

The catalase may be added at any timing if it takes place after the sterilizing composition is used in the sterilizing unit 4 but before it is fed to the heating unit 3. Preferably, however, the catalase is added in the circulating tank 1 or in the recovering tank 5 as shown in FIGS. 1 and 2. In the embodiment shown in FIG. 1, an enzyme tank 7 in which the catalase is adjusted is connected to the circulating tank 1 through a valve 11, and the additional catalase is suitably fed into the circulating tank 1 depending on the concentrations of the peracetic acid-type sterilizing composition solution and the catalase in the circulating tank 1. In the embodiment shown in FIG. 2, the enzyme tank 7 is connected to the recovering tank 5 through a valve 11, and the catalase is fed into the recovering tank 5.

(Peracetic Acid-Type Sterilizer (Undiluted Solution))

As the peracetic acid-type sterilizer (undiluted solution) used for the sterilizing composition solution of the invention, there can be used any conventionally known one at any concentration. Preferably, there can be used a peracetic acid-type sterilizer comprising 10 to 25% by weight of peracetic acid, 20 to 40% by weight of acetic acid, 15 to 25% by weight of hydrogen peroxide, and the remainder being water and, as required, a stabilizer.

As the peracetic acid-type sterilizer, there can be exemplified the Oxyper 100 (manufactured by Nihon Peroxide Co., and comprises 10.2% by weight of peracetic acid, 20.6% by weight of acetic acid and 17.2% by weight of hydrogen peroxide). The peracetic acid-type sterilizer is used with its concentration being diluted and adjusted with water.

(Catalase)

The catalase is an enzyme that decomposes the hydrogen peroxide. In the present invention, it is important that the catalase has resistance in an acidic region, i.e., in a region of pH 2.6 to 6.0 in the peracetic acid-type sterilizer. It is allowable to use either a catalase stemming from fungi or a catalase stemming from bacteria. Specifically, however, it is desired to use the catalase stemming from fungi and, particularly, to use the catalase stemming from *Aspergillus niger*. The catalase may be used in one kind only or in a plurality of kinds being mixed together.

Further, in the invention as described above, the catalase is added (supplemented) to the sterilizing composition solution under the condition of a relatively high temperature. It is, therefore, desired that the catalase has heat resistance and chemical resistance (resistance against the peracetic acid). Concretely, it is desired to use the catalase capable of decomposing the hydrogen peroxide by not less than 35% of its initial concentration 10 minutes after it has been added to the peracetic acid-type sterilizer adjusted at a temperature of 50° C. so as to have a peracetic acid concentration of 3000 ppm.

As the catalase, though not limited thereto only, there can be used commercially available catalase enzyme preparations, such as LEONET F PLUS (produced by Nagase Chemtechs Co.) and ASKU-Super 25 (produced by Mitsubishi Gas Chemicals Co.).

In the invention, there is no particular limitation on the catalase that is used; i.e., the catalase may be in any form such as solution, powder, or in a form fixed to a water-insoluble substrate such as beads.

Further, the commercially available catalase enzyme preparations, usually, contain sodium chloride. To prevent the pipes from being corroded with the chlorides, therefore, it is desired that the catalase enzyme preparations are used with the concentration of chloride ions therein being lowered by a known desalting method.

The catalase may be added (supplemented) in a required amount at one time to the sterilizing composition solution in the circulating tank 1 or in the recovering tank 5. Preferably, however, the catalase is added in its whole amount being divided into a plurality of times. This enables the catalase to mildly decompose the hydrogen peroxide and to more reliably suppress the foaming caused by the catalase.

(Sterilizing Composition Solution)

In the sterilizing method of the present invention, the sterilizing composition solution that is to be circulated is prepared by adding a pH-adjusting agent, water and catalase to the peracetic acid-type sterilizer which is an undiluted solution containing the above-mentioned peracetic acid, acetic acid and hydrogen peroxide in an equilibrium state.

The preparation method consists of adding the pH-adjusting agent to the peracetic acid-type sterilizer having a desired peracetic acid concentration based on a prerequisite that the concentration of the peracetic acid would lie in a range described below after having been diluted with water in order to adjust the pH to lie in a range of 2.6 to 5.0 and, thereafter, adding the catalase such that the concentration thereof is 0.1 to 10 μg/mL and, specifically, 0.1 to 3.0 μg/mL. The order to adding the pH-adjusting agent and the catalase is not necessarily limited as described above. However, by adding them in the order as described above, the activity of the catalase can be maintained at its maximum degree.

It is desired that the sterilizing composition solution used in the invention is such that the catalase added thereto accelerates the decomposition of the hydrogen peroxide so that the concentration of the hydrogen peroxide is maintained to be less than 500 ppm in at least the circulating tank 1 and, desirably, in the whole circulating passage and that the concentration of the peracetic acid is maintained in a range of 500 to 10,000 ppm and, specifically, 1,000 to 3,500 ppm making it, therefore, possible to maintain excellent sterilizing power.

The peracetic acid-type sterilizing composition solution of the invention also contains the acetic acid. When the peracetic acid concentration lies in the above range, it is desired that the concentration of the acetic acid lies in a range of 1,000 to 40,000 ppm.

As described above, further, the catalase used in the invention should be so selected as to exhibit its activity over a pH range of 2.6 to 6.0. In the peracetic acid-type sterilizing composition liquid, however, if pH exceeds 5.0, the peracetic acid undergoes the decomposition and its concentration decreases to exhibit decreased sterilizing power.

It is, further, desired to so select the catalase as to exhibit its activity over a pH range of 3.0 to 6.0 to most effectively work to decompose the hydrogen peroxide. Here, in order for the peracetic acid to most effectively exhibit its sterilizing effect, it is desired that the peracetic acid-type sterilizing composition solution has a pH of not higher than 4.0.

From the above point of view, the pH of the sterilizing composition solution is maintained to be 2.6 to 5.0 and, specifically, 3.0 to 4.0. This enables the peracetic acid-type sterilizing composition solution to work as a sterilizer without losing stability, maintaining activity of the catalase and exhibiting the action for decomposing the hydrogen peroxide to a sufficient degree despite it is added in small amounts.

In the invention, as the pH-adjusting agent used for bringing the pH of the peracetic acid-type sterilizing composition to lie in the above-mentioned range, there can be used a known alkaline composition such as sodium hydroxide or potassium hydroxide.

For adjusting the concentration of the peracetic acid-type sterilizing composition solution in the circulating tank 1, further, the sterilizing composition solution fed from the buffer tank 9 may be the sterilizing composition solution having the concentration of hydrogen peroxide, concentration of peracetic acid and pH lying over the above-mentioned ranges. Particularly, however, it is desired to use the sterilizing composition solution having a concentration of hydrogen peroxide as low as possible and having a high concentration of peracetic acid.

It is also allowable to add the catalase into the buffer tank 9 so as to introduce it into the circulating tank 1 together with the sterilizing composition solution impairing, however, the activity of the catalase since the sterilizing composition solution has a high concentration of peracetic acid in the buffer tank 9. Further, the amount of the hydrogen peroxide increases if the peracetic acid-type sterilizing composition solution is heated. It is, therefore, necessary to add the catalase to the peracetic acid-type sterilizing composition solution when it is being heated. Namely, the catalase must be added in the circulating passage of after the sterilizing composition solution was used but before it is being fed into the heating unit. It is, specifically, desired that the catalase is added in the circulating tank 1 or in the recovering tank 5.

(Sterilizing Method)

In the sterilizing method of the present invention, the above-mentioned sterilizing composition solution is heated at a temperature of 40 to 75° C. and, specifically, 50 to 65° C. through the heating unit and is fed to the sterilizing unit so as to be applied onto the surfaces of the materials to be sterilized, such as containers. The materials to be sterilized may be a variety of kinds of known containers such as cans, bottles and plastic containers, as well as caps.

If the temperature of the sterilizing composition solution is higher than the above range, decomposition of the peracetic acid tends to be accelerated and, besides, proteins stemming from the catalase aggregate to clog the nozzles. If the temperature of the sterilizing composition solution is lower than the above range, on the other hand, the sterilizing power decreases, an extended period of time is required for the sterilization, and the sterilizing efficiency decreases.

By bringing the sterilizing composition solution adjusted at the above temperature into contact for 5 to 10 seconds, it is allowed to obtain the sterilizing capability of a sterilizing level of not lower than 5D.

After the sterilization, the sterilized materials (containers) are taken out from the sterilizing unit and are sent to the next step of washing where they are washed with aseptic water to remove the sterilizing composition solution remaining on the surfaces of the containers. Here, the sterilizing composition solution used in the sterilizing method of the present invention has a concentration of the hydrogen peroxide of as low as 500 ppm or less. Despite of the washing is conducted for only a short period of time, therefore, no hydrogen peroxide remains on the surfaces of the bottles and hygienic conditions are not impaired.

Further, the catalase that is used in suppressed amounts little causes the foaming that stems from the decomposition of the hydrogen peroxide, little causes the fouling of the unit that stems from the adhesion of aggregated matters on the storage tank and the like and, therefore, enables the sterilizing operation to be continued requiring the washing of only a short period of time.

EXAMPLES (Measuring the Components of the Sterilizing Composition Solution)

1. Concentration of the Peracetic Acid.

After the catalase reaction has been finished, measurement was taken by the potassium permanganate-iodine method. That is, the sample was titrated with the potassium permanganate in an acidic condition with the sulfuric acid to measure the concentration of the hydrogen peroxide. Thereafter, the potassium iodide and a starch indicator were added, and the sample was titrated with the sodium thiosulfate to measure the concentration of the peracetic acid.

As for the reaction ending time of catalase, measurement was taken for every 5 minutes after 5 minutes have passed from when the catalase was added to the sterilizing composition solution, and a moment when there was seen no decrease in the concentration of the hydrogen peroxide was regarded to be the end of the reaction while taking measurement with the passage of time, and the concentrations of the components were thus measured.

2. Concentration of the Hydrogen Peroxide.

There are two concentrations of the hydrogen peroxide, i.e., the one after the peracetic acid type sterilizer was diluted with water but before adding catalase thereto (diluted concentration calculated from the undiluted concentration of the peracetic acid type sterilizer) and the concentration measured after the catalase reaction has been finished. Measuring method complies with the measurement of the peracetic acid concentration described in 1. above.

(Method of Evaluation)

1. Power for Decomposing the Hydrogen Peroxide.

The concentration ($I_O$) of the hydrogen peroxide immediately after the preparation of the sterilizing composition solution and the concentration (I) of the hydrogen peroxide after 10 minutes have passed from the start of the preparation, were measured, and a ratio of reduction $[(I_0-I)/I_0] \times 100$ (%/10 min.) was calculated.

2. Sterilizing Effect.

By using a 500-ml polyethylene terephthalate bottle (hereinafter referred to as bottle), a bacteria solution of *Bacillus cereus* ATCC 9139 was prepared as sample bacteria. By using a sprayer, the sample bacteria were uniformly sprayed onto the inner surface of the bottle such that the density thereof was $10^6$ cfu/bottle, and the bottle was dried to obtain a bottle for evaluation. Next, the sterilizing solution immediately after the catalase reaction was adjusted at a temperature of 50° C. or 65° C., and was sprayed into the bottle for evaluation so as to come in contact therewith for 8 seconds. Thereafter, the inner surface of the bottle was washed with pasteurized water. The pasteurized water used for the washing was measured for its number of living bacteria by using a standard agar culture medium based on a membrane filter method. From the initial number of bacteria and the number of bacteria that are living, the sterilizing effect (D) was found according to the following formula. The number of times of testing was n=3, and the sterilizing effect was evaluated regarding the average number of living bacteria as the number of living bacteria.

$$D=LOG(N_0/N)$$

wherein $N_0$ is the initial number of bacteria, and N is the number of living bacterial.

If the D-value was not less than 6D, the sterilizing effect was high and was evaluated to be ○, if the D-value was not less than 5D but was less than 6D, the sterilizing effect was observed and was evaluated to be Δ and if the D-value was less than 5D, the sterilizing effect was low and was evaluated to be X.

Examples 1, 3 and 5

How the addition of the catalase and the concentration of the hydrogen peroxide would affect the sterilizing power was examined.

A peracetic acid-type sterilizer (trade name: Oxyper 100, manufactured by Nihon Peroxide Co.: peracetic acid 10.2 wt %, acetic acid 20.6 wt %, hydrogen peroxide 17.2 wt %) was diluted with water in the preparation tank so that the concentration of the peracetic acid was 10,000 ppm, and the LEONET F PLUS (manufactured by Nagase Chemtechs Co.) was added thereto as the catalase in an amount of 0.4 μg/mL to decompose the hydrogen peroxide into 0 ppm to thereby prepare a sterilizing composition solution of a high concentration.

Next, the sterilizing composition solution of the high concentration was diluted with water in the circulating tank to adjust the concentration of the peracetic acid to be 1500 ppm, and was circulated through the passage shown in FIG. 1.

The sterilizing composition solution was heated through the heating unit at two temperatures of 50° C. and 65° C. The sterilizing composition solution that was heated at 50° C. was circulated for 12 hours and 24 hours while the sterilizing composition solution that was heated at 65° C. was circulated for 6 hours. The concentration of the peracetic acid while the sterilizing composition solution was in circulation was maintained at 1500 ppm by adding thereto the above-mentioned sterilizing composition solution of the high concentration from the buffer tank.

After the passage of the above-mentioned periods of time, the LEONET F PLUS was added to the sterilizing composition solution in the circulating tank so that the concentration of the catalase was 0.4 μg/mL. After 10 minutes have passed from the addition, the concentration of the hydrogen peroxide and the sterilizing effect were confirmed as shown in Table 1.

Examples 2, 4 and 6

The sterilizing composition solutions were prepared in the same manner as in Examples 1, 3 and 5 but using the ASKU-Super 25 (manufactured by Mitsubishi Gas Chemicals Co.) as the catalase and adding it in an amount of 5 μg/mL in the preparation tank. After 10 minutes have passed from the addition of the catalase, the concentration of the hydrogen peroxide and the sterilizing effect were confirmed as shown in Table 1.

Comparative Examples 1 to 3

The sterilizing composition solutions were prepared in the same manner as in Examples 1, 3 and 5, and were circulated without, however, adding the catalase. The concentration of the hydrogen peroxide and the sterilizing effect were confirmed as shown in Table 1.

heated at 50° C. and was measured for its concentration of hydrogen peroxide. Next, as the catalase, the LEONET F PLUS or the ASKU-Super 25 was added in an amount of 0.4 μg/mL. After 10 minutes have passed, the concentration of the hydrogen peroxide was measured again to calculate the rate of decomposition as shown in Table 2.

TABLE 2

| Trade name of catalase | Hydrogen peroxide concentration (ppm) | | Rate of decomposition |
|---|---|---|---|
| | After 0 min. | After 10 min. | |
| ASKU-Super 25 | 5032 | 3655 | 27% |
| LEONET F PLUS | 5015 | 170 | 97% |

INDUSTRIAL APPLICABILITY

According to the sterilizing method of the present invention, it is made possible to use, in a circulating manner, the peracetic acid-type sterilizing composition solution maintaining its sterilizing power without the need of cooling the sterilizing composition solution as a result of suppressing a decrease in the activity of the catalase saving, therefore, the heat energy. Therefore, the sterilizing method of the invention can be favorably utilized for aseptically filling the mass-produced products such as polyethylene terephthalate bottles and the like containers.

DESCRIPTION OF REFERENCE NUMERALS 1 circulating tank
2 feed pump
3 heating unit
4 sterilizing unit
5 recovery tank
6 feed pump
7 enzyme tank
8 feed pump
9 buffer tank
10 preparation tank
11 valve
12 valve
13 valve

TABLE 1

| | Temp. of sterilizing solution (° C.) | Sterilizing solution continuously heated for (hrs) | Addition of catalase | | Hydrogen peroxide concentration (ppm) | | Sterilizing effect |
|---|---|---|---|---|---|---|---|
| | | | Yes/no | Trade name | Before added | After added | |
| Ex. 1 | 50 | 12 | yes | LEONET F PLUS | 578 | 75 | ○ |
| Ex. 2 | | | yes | ASKU-Super 25 | 580 | 387 | ○ |
| Comp. Ex. 1 | | | no | — | 578 | 580 | X |
| Ex. 3 | | 24 | yes | LEONET F PLUS | 816 | 122 | ○ |
| Ex. 4 | | | yes | ASKU-Super 25 | 818 | 490 | Δ |
| Comp. Ex. 2 | | | no | — | 816 | 819 | X |
| Ex. 5 | 65 | 6 | yes | LEONET F PLUS | 685 | 137 | ○ |
| Ex. 6 | | | yes | ASKU-Super 25 | 683 | 486 | Δ |
| Comp. Ex. 3 | | | no | — | 685 | 689 | X |

(Experiment 1)

The catalase was examined for its resistance against the heat and against the chemicals.

A peracetic acid-type sterilizer (pH 2.67) prepared by so diluting the peracetic acid-type sterilizer (Oxyper 100) that the concentration of the peracetic acid was 3000 ppm, was

The invention claimed is:

1. A sterilizing method which comprises circulating a sterilizing composition solution containing peracetic acid, hydrogen peroxide, acetic acid and catalase in a circulating passage, said circulating passage comprising a circulating tank, a heating unit and a sterilizing unit, said circulating comprises preparing the sterilizing composition in the circulating tank, then heating the sterilizing composition through the heating unit, then feeding the heated sterilized composition to the sterilizing unit, and then recovering the sterilizing composition in the circulating tank after using the sterilizing composition solution for sterilization, wherein the sterilizing composition solution prepared in said circulating tank is a sterilizing composition solution containing the catalase at a concentration of 0.1 to 10 µg/ml, the peracetic acid at a concentration of 500 to 10000 ppm, and the hydrogen peroxide at a concentration of less than 500 ppm, the sterilizing composition solution recovered from said sterilizing unit is recovered in the circulating tank without being cooled, and the catalase is added to the sterilizing composition solution in the circulating passage after leaving the sterilization unit but before being fed to the heating unit.

2. The sterilizing method according to claim 1, wherein said catalase is a catalase capable of decomposing the hydrogen peroxide by not less than 35% of its initial concentration of the hydrogen peroxide 10 minutes after addition of 0.4 µg/ml of the catalase to the peracetic acid-type sterilizer adjusted at a temperature of 50° C. so as to have a peracetic acid concentration of 3000 ppm.

3. The sterilizing method according to claim 1, wherein said catalase is added in the circulating tank.

4. The sterilizing method according to claim 1, wherein the catalase is added in a recovery tank arranged between the sterilizing unit and the circulating tank within the circulating passage.

* * * * *